United States Patent [19]

Di Napoli

[11] Patent Number: 5,670,695
[45] Date of Patent: Sep. 23, 1997

[54] PROCESS FOR THE PREPARATION OF DIACEREIN

[75] Inventor: Guido Di Napoli, Collonge-Bellerive, Switzerland

[73] Assignee: Laboratoire Medidom S.A., Geneva, Switzerland

[21] Appl. No.: 376,722

[22] Filed: Jan. 23, 1995

[51] Int. Cl.$^6$ ............ C07F 9/02; C07C 333/00; C07C 49/593

[52] U.S. Cl. ............ 560/76; 560/239; 560/131; 552/262

[58] Field of Search ............ 560/239, 255, 560/131, 139; 552/262; 549/417; 514/548

[56] References Cited

U.S. PATENT DOCUMENTS

| | | |
|---|---|---|
| 4,244,968 | 1/1981 | Friedmann . |
| 4,346,103 | 8/1982 | Friedmann ............ 424/308 |
| 4,950,687 | 8/1990 | Dall'Asta et al. ............ 514/548 |
| 5,391,775 | 2/1995 | Carcasona et al. ............ 552/262 |
| 5,393,898 | 2/1995 | Carcasona et al. ............ 552/262 |

FOREIGN PATENT DOCUMENTS

| | | |
|---|---|---|
| 875945 | 8/1979 | Belgium . |
| 2508798 | 4/1986 | France . |

OTHER PUBLICATIONS

Sostanze Farmaceutiche, Axel Kleemann–Jurgen Engel, Organizzazione Editoriale Medico Farmaceutica, S.r.l. 1988.

The Merck Index, 11 Ed., Merck & Co., Inc. 1989, pp. 467, 351, 1300.

Advanced Organic Chemistry—Reactions, Mechanisms and Structure, J. March, John Wiley & Sons, 3rd Ed., 1985, pp. 346–347 and 1084.

Fairbairn et al., *J. Pharm. Sci.*, 66 (9), pp. 1300–1303 (1977).

*Primary Examiner*—Jose G. Dees
*Assistant Examiner*—Karl J. Puttlitz, Jr.
*Attorney, Agent, or Firm*—Kenyon & Kenyon

[57] ABSTRACT

The present invention relates to a process for the preparation of 1,8-diacetoxy-3-carboxyanthraquinone, also known as diacerein, via aloin acetylation, oxidation of the acetylated product, and purification of the raw diacerein obtained by means of crystallization from 2-methoxyethanol or N,N-dimethylacetamide and optionally by dissolution of the corresponding salt with triethylamine in methylene chloride, followed by removal of the insoluble residue.

30 Claims, No Drawings

PROCESS FOR THE PREPARATION OF DIACEREIN

FIELD OF THE INVENTION

The present invention relates to a process for the preparation of 1,8-diacetoxy-3-carboxyanthraquinone, also known as Diacerein (I)

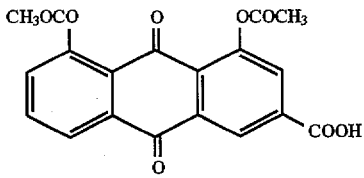

Diacerein is a compound possessing antiarthritic activity, available under various trademarks, e.g. Artrodar® (The Merck Index, 11th Ed., 1989, Merck & Co., Inc., Rahaway, N.J., USA, 2939).

PRIOR ART

French Pat. No. 2,508,798-B1 and Belgian Pat. No. 875,945 disclose the preparation of diacerein via dissolution of 1,8-dihydroxyanthraquinone-3-carboxylic acid in excess acetic anhydride, in the presence of sulphuric acid as a catalyst.

1,8-Dihydroxy-anthraquinone-3-carboxylic acid occurs either free or as a glucoside in several plants, e.g. in Senna leaves. It is also prepared from chrysophanic acid diacetate (The Merck Index, 11th Ed., 1989, Merck & Co., Inc., Rahaway, N.J., USA, 8175 and 2263) and by oxidating of the corresponding 3-hydroxymethyl derivative, i.e. 1,8-dihydroxy-3-hydroxymethylanthraquinone (aloe-emodin), with chromic anhydride ("Sostanze formaceutiche", a translation into Italian and revision by R. Longo, OEMF, Milano, 1988, p. 596 of "Pharmazeutische Wirkstoffe, Synthesen, Patente, Anwendungen", A. Kleemann, J. Engel, George Thieme Verlag, Stuttgart-New York, 1982–1987).

However, the diacerein obtained by means of the processes of the prior art contains—as a by-product—considerable amounts of the aforesaid aloe-emodin derivative, which has mutagenic activity even in amounts as low as 70 ppm.

Therefore, the need for a process producing diacerein in high yields and especially free from said impurities was deeply felt.

DETAILED DESCRIPTION OF THE INVENTION

The Applicant has found a new process for the preparation of 1,8-diacetoxy-3-carboxyanthraquinone, which can be advantageously used instead of the methods already known.

Said process comprises:

a) acetylation of aloin (II):

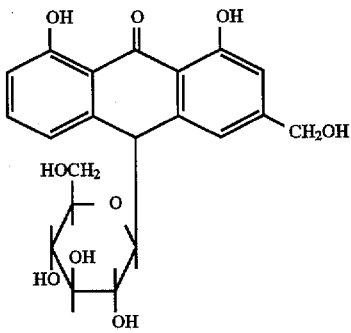

by treatment with an acetylating agent in an appropriate diluent to obtain an acetylated product as per formula (III)

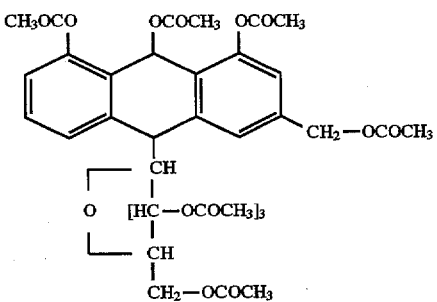

b) treatment of acetylated product (III) with an oxidizing agent to give raw diacerein;

c) purification of raw Diacerein.

Aloin, a natural substance isolated from various species of aloe, consists almost exclusively of barbaloin (10-β-glucopyranosyl-1,8-dihydroxy-3-hydroxymethyl-anthracen-9-one). Due to its purgative properties, it is used for said purpose especially in veterinary practice.

The aloin used in the present invention is a commercially available product.

The acetylating and oxidizing agents of the present process can be chosen among those known to the man skilled in the art, it being understood that the oxidizing agent must be one of those capable of oxidizing primary alcoholic functions to carboxylic acids. To this purpose, we refer to a comprehensive text of organic chemistry, such as "Advanced Organic Chemistry—Reactions, Mechanisms and Structures", Jerry March, John Wiley & Sons, 3rd Ed., 1985 (cf., in particular, paras. 0–22 and 0–23, pages 346 and 347; para. 9–22, page 1084).

In the preferred embodiment of the present invention, the acetylating agent is acetic anhydride.

The acylating agent may be in a stoichiometric proportion to aloin or in excess of the stoichiometric and, in this case, may be used e.g. as a reaction solvent.

In acetylation, various organic solvents may be utilized as diluents, provided they are inert, such as for example methylene chloride, or in any case compatible with the reaction conditions, such as glacial acetic acid.

In the present invention acetic anhydride is preferably used as a diluent, its cost being fairly low.

Acetylation with acetic anhydride is generally carried out in the presence of bases (sodium acetate, aromatic amines, such as pyridine, aliphatic amines, such as triethylamine) or of acids, such as sulphuric acid, as catalyst.

More preferably, in the present invention sodium acetate is used, generally in amounts varying from 1% to 10% in moles in respect of the substrate to be acetylated.

In the present invention acetylation is carried out at a temperature ranging from +30° C. to +150° C. and, when acetic anhydride is used as a solvent, preferably at the boiling temperature of the reaction mixture (138°–139° C.).

The choice of the "oxidizing system"—this expression being used herein to mean the oxidizing agent and the reaction medium collectively—is critical, since undesired reactions, such as the hydrolysis of acetate groups, are to be reduced to a minimum.

The preferred oxidizing system of the present process is chromic anhydride in glacial acetic acid.

In the present process, when chromic anhydride in glacial acetic acid is used, the operating temperature preferably ranges from 0° C. to +100° C., and more preferably from +20° C. to +70° C.

Chromic anhydride is preferably used in amounts ranging from 5 to 15 moles/mole of starting aloin, and more preferably from 7 to 9 moles/mole of starting aloin.

In a particularly preferred embodiment of the present invention, the oxidation step is carried out after acetylation, without isolating the acetylated intermediate.

More particularly, the reaction mixture coming from the acetylation is filtered and added at a temperature from +60° C. to +70° C. with a mixture prepared mixing water (in an amount not exceeding the stoichiometric amount of the acetic anhydride present in the reaction medium, typically about half the stoichiometric amount of the acetic anhydride), with chromic anhydride and glacial acetic acid. Typically, after about 3 hours at +60°–+70° c., the reaction mixture is cooled to +20° C.–+25° C., kept at this temperature for at least 6 hours, the diacerein is recovered by centrifugation, washed with aqueous acetic acid solutions and dried.

The purification of raw diacerein according to the present process is characterized by being effected by means of at least one crystallization step from a solvent selected from 2-methoxyethanol and N,N-dimethyl acetamide.

The Applicant has unexpectedly found that using these solvents it is possible to drastically drift downwards the aloe-emodin content below 70 ppm. This is a very interesting result, since aloe-emodin is an impurity considered as mutagenic beyond this value. The purification of Diacerein optionally comprises a salification step, carried out by treating diacerein with an aliphatic tertiary amine, e.g. triethylamine, in an organic solvent capable of dissolving the diacerein salt with said organic base, e.g. an halogenated hydrocarbonic solvent such as methylene chloride.

Triethylamine is generally used in amounts ranging from 1 to 1.3 moles/mole diacerein to be purified and, in any case, in amounts adequate for diacerein complete dissolution.

The diacerein salt solution obtained is filtered, so as to eliminate the insoluble residue and the corresponding acid is precipitated by acidification in aqueous medium and collected.

In the present process, diacerein salification and collection are preferably carried out at a temperature of from +15° C. to +30° C.

Acidification is preferably carried out by adding the diacerein salt organic solution to an aqueous mixture of acetic acid and hydrochloric acid, where diacerein precipitates at the operating temperature.

Typically, the filtered organic solution containing the triethylamine salt of diacerein is added with aqueous concentrated hydrochloric acid, in an amount adequate for diacerein precipitation, then the precipitated diacerein is collected, washed with aqueous acetic acid and with water, and dried.

Diacerein can be air dried at 70°–80° C.

The raw diacerein coming from the oxidation step is typically dried up to a water content lower than 1%.

Before the crystallization steps, diacerein is suitably dried up to a loss on drying value below 0.5%.

According to a particularly preferred embodiment of the present invention, the raw diacerein coming from the oxidation step is first subjected to said salification step by treating it with triethylamine in methylene chloride as the halogenated solvent, then to crystallization from 2-methoxyethanol, and finally to crystallization from anhydrous N,N-dimethylacetamide.

According to a further preferred embodiment of the present invention, the purification is effected by subjecting diacerein to three successive crystallizations from anhydrous N,N-dimethylacetamide, optionally in admixture with acetic anhydride, then to crystallization from ethanol.

The crystallization from ethanol decreases below 1500 ppm the dimethylacetamide content of the purified diacerein.

More preferably, the three successive crystallizations from N,N-dimethylacetamide are carried out using mixtures of anhydrous N,N-dimethylacetamide and acetic anhydride in ratio 400:6 weight/weight. Ethanol has preferably a maximum moisture content of 5%.

Typically, anhydrous N,N-dimethylacetamide has a water content lower than 0.2%.

N,N-dimethylacetamide with a water content between 0.2 and 3% can be treated with acetic anhydride (6.6 Kg per liter of water) at room temperature, before heating the solvent/diacerein mixture as required in the crystallization step.

In the present crystallization steps, diacerein is typically dissolved in the selected solvent by heating the solvent/diacerein mixture (generally to temperatures of about +75°–+125° C., then it is precipitated by cooling the organic solution so obtained (generally to temperatures of about 0°–+5° C.).

The process claimed herein gives high yields of highly pure diacerein, which can be directly used for the preparation of pharmaceutical compositions. In particular, by means of the aforesaid purification of diacerein it is possible to reduce the aloe-emodin mutagen content to values below 20 ppm.

The following examples are conveyed by way of indication, not of limitation of this invention.

ALOIN

The aloin used as starting material was an odourless yellow-greenish powder becoming darker by exposure to the light.

Its chemico-physical properties are reported below:

Solubility: almost completely soluble in water (1:130), in alcohol (1:20), soluble in acetone.

Identification: IR spectrum in nujol corresponding to that of a reference sample.

Loss on drying: at 60° C. for 3 hrs, 3% max. of the initial weight.

Sulphuric ashes content: evaluated on 1 g of product, 0.2% max.

Acidity: the product was mixed with 100 ml of water and filtered through paper filter. The pH of the filtrate was measured.

Acceptable values: from 4.5 to 5.5.

Insolubles in water: 1 g (W=weight) of the product under examination and 5 ml of water were mixed in a mortar; the resulting mixture was added with 15 ml of water and mixing was continued.

The mixture was put into a 250 ml becker and quantitatively diluted with 100 ml of water. The mixture was stirred for 2 hrs at 25° C., then it was filtered through a tared filter (T=tare) and the residue was dried under vacuum at 70° C. for 3 hrs. The resulting product was cooled and weighed again (G=dry product gross weight). The insoluble residue per cent was determined by the following formula:

$$\frac{G-T}{W} \times 100$$

Acceptable values: 1.5% max.

α- AND β-BARBALOIN CONTENT

Assay: HPLC system consisting of Hypersil® 50DS column (250×4.6 mm); eluent: water-acetonitrile, 80:20 v/v; flow rate: 2 ml/min; detection: 295 nm.

The following solutions were prepared:

A) Exactly weighed 0.2 g of the product under examination was diluted to 20 ml with methanol. 2 ml of the resulting solution was diluted to 20 ml with the same solvent (solution test).

B) Exactly weighed 0.15 g of α-barbaloin was diluted to 20 ml with methanol. 2 ml of the resulting solution was diluted to 20 ml with the same solvent.

20 mcl of solution A and, respectively, of solution B were injected into the HPLC column.

The response factors of α- and β-barbaloin were considered identical.

$$\text{Response factor} = \frac{A_{so} \times 100 \times 100}{W_{st} \times A \times (100 - M)}$$

$$\alpha\text{-barbaloin \%} = \frac{A_s \times 100}{F \times W_s}$$

$$\beta\text{-barbaloin \%} = \frac{A_s \times 100}{F \times W_s}$$

where $A_{so}$=mean of the areas of solution B
$W_{st}$=standard sample weight (mg)
A=standard sample area
M=standard sample moisture
$A_s$=area of the peak of the sample under examination
F=response factor
$W_s$=weight of the sample under examination Acceptable values: 90% min. as a sum of α- and β-barbaloin, determined on the basis of the anhydrous product.

EXAMPLE 1 i) Preparation of Raw Diacerein

A glass-lined 1500 l reactor was fed with 75 kg aloin, 75 kg anhydrous sodium acetate, and 708.8 kg acetic anhydride.

The mixture was heated to reflux (138° C.) and maintained at said temperature for 20 min. Then it was cooled to 40° C. and filtered through a pressure filter. The solution was collected in a glass-lined 3000 l reactor. The 1500 l reactor and the filter were washed with 488.8 kg acetic anhydride, and the wash water was collected in said 3000 l reactor.

While maintaining the temperature at 60° C. to 70° C., the solution was added, over a time of 3–3½ hrs, with a solution prepared as follows: a glass-lined 1500 l reactor was fed with deionized water (81.32 kg) and, at a temperature of 30° C. max., with chromic anhydride (135.54 kg) and glacial acetic acid (1137.5 kg). Once the addition was completed, the temperature was maintained at 60° C. to 70° C. for 3 hrs, then lowered to 20°–25° C. and maintained at said value for 6 hrs at least. The product was centrifuged under a stream of nitrogen and the mother liquors were collected in an appropriate container. The product was washed with 50% acetic acid (150 kg) and the wash waters were collected with the mother liquors. The product was washed twice again with 1% acetic acid solution (1050 kg each time), and the wash waters were fed to the purification plant. The product was discharged from the centrifuge and air dried at 70° C. to 80° C.

By this method, diacerein average yield was of 52.5 kg.

The product obtained was a odourless microcrystalline yellow powder with a water content lower than 1%. (Karl Fischer method).

ii) Raw Diacerein Preliminary Purification

A glass-lined 1500 l reactor was fed with raw diacerein (100 kg) and methylene chloride (626.7 kg) (commercial or recovered methylene chloride may be used).

While maintaining the temperature at 18° C. to 22° C., triethylamine (26.33 kg) was added to obtain a pH value of 8 and complete dissolution.

The resulting solution was filtered into a glass-lined 3000 l reactor, previously fed with deionized water (212 kg) and 80% acetic acid (108 kg), while the temperature was maintained at 18° C. to 22° C. The 1500 l reactor and the filter were washed with methylene chloride (83.33 kg) and the solution was collected in the 3000 l reactor. A 32% approx. (w/w) hydrochloric acid aqueous solution (6.67 kg) was added and the resulting mixture was agitated for 2 hrs at 18° C. to 22° C. The product was centrifuged and the mother liquors were collected in an appropriate container. The product was repeatedly washed with 80% acetic acid (200 kg) and then with plenty of deionized water so as to secure chloride ions elimination from the wash waters.

The product obtained was air dried at 70° C. to 80° C.
The product loss on drying was lower than 0.5%.

By this purification method, diacerein average yield was of 85 kg.

iii) Diacerein Purification with Methyl Cellosolve®

A glass-lined 1500 l reactor was fed with diacerein purified as described under ii) (130 kg) and Methyl Cellosolve® (698.15 kg) (trademark of 2-methoxyethanol) either fresh or recovered. The mixture was heated to reflux for 3 hrs. Then it was cooled to +5° C. and maintained at said temperature for 1 hr.

The product was centrifuged and the mother liquors were collected in an appropriate container. The product was washed with Methyl Cellosolve® (216.7 kg) and then with plenty of deionized water. The product obtained was air dried at 70° C. to 80° C.

The product loss on drying was 0.5% max.

By this purification method, diacerein average yield was of 121.5 kg.

iv) Diacerein Purification with Dimethyl Acetamide

A glass-lined 1500 l reactor was fed with diacerein purified as described under iii) (120 kg) and anhydrous dimethyl acetamide (242.4 kg), either fresh or recovered. Recovered dimethyl acetamide containing 0.2 to 3% of water can be used if added with 6.6 kg of acetic anhydride/liter of water and maintaining the dimethyl acetamide-diacerein mixture under agitation for 1 hr at 25° C. to 30° C. before raising the temperature to 110° C.

The mixture was heated to 110° C. and maintained at said temperature for 30 min. After cooling to 0° C., the product obtained was centrifuged and mother liquors were collected in an appropriate container. The product was washed with dimethyl acetamide (19.2 kg) and then with deionized water (684 kg). The resulting product was fed to a glass-lined 2000 l reactor together with deionized water (1714.2 kg). The product was agitated for 1 hr at room temperature, centrifuged, and washed six times with deionized water (68.52 kg each time).

The product obtained was air dried at 70° C. to 80° C.

By this crystallization method, diacerein average yield was of 112 kg.

The structure of the product obtained was determined by the following analytical data:

A) IR Spectrum

The IR spectrum of diacerein dispersed in KBr shows
- a series of bands in the range between 3300 and 2400 $cm^{-1}$ which are attributable to the stretching vibrations of the —OH of the carboxylic group;
- a series of bands in the range between 3100 and 3000 $cm^{-1}$ which are attributable to the stretching of the aromatic CH groups;
- a band at 2930 $cm^{-1}$ attributable to the stretching of the $CH_3$ groups;
- a band at 1769 $cm^{-1}$ attributable to the two carboxylic groups of the acetate groups;
- two peaks at 1690 and 1679 $cm^{-1}$ attributable to the stretching of the carbonyl groups of the benzoquinone ring and of the carboxylic group;
- a band in the range between 1210 and 1025 $cm^{-1}$ attributable to the acetate group;
- a signal at 1369 $cm^{-1}$ attributable to the asymmetric deformation of the $CH_3$ groups;
- a band at 1450 $cm^{-1}$ attributable to the asymmetric deformation of said groups.

B) $^1$H-NMR Spectrum

The spectrum was run in deuterated dimethyl sulphoxide ($d_6$-DMSO) and showed:
- an absorption between 8.6 and 7.6 δ (ppm) (5H) attributable to aromatic hydrogens;
- a very broad signal at about 4.40 δ (ppm) (1H) attributable to the proton of the carboxylic function;
- a singlet at 2.40 δ (ppm) (6H) attributable to the 6 protons of the two $CH_3$ groups of the acetyl groups.

C) Elemental Analysis

The values found correspond to the theoretical ones:

|   | Found (%) | Theoretical (%) |
|---|-----------|-----------------|
| C | 61.83     | 61.95           |
| H | 3.34      | 3.26            |

EXAMPLE 2 i) Raw Diacerein is Prepared as Described in Example 1 i) and Purified as Follows ii) Diacerein First Purification Charge a 1500 l glass lined vessel with kg 100 of crude diacerein, kg 400 of virgin (fresh and anhydrous) or recovered dimethylacetamide and kg 6 of acetic anhydride. If recovered dimethylacetamide with moisture between 0.3% and 2% is used, add kg 6.6 of acetic anhydride for each kg of water contained in dimethylacetamide. Stir for 30 minutes at 25°–30° C., heat up to 100° C. and keep this temperature for 15 minutes. Cool to 0°–2° C., keep this temperature for 2 hours and centrifuge the product, collecting mother waters into a proper container. Wash with kg 60 of cooled virgin or recovered dimethylacetamide with maximum moisture of 5%, then abundantly with deionized water to eliminate at the most dimethylacetamide.

The product so obtained is dried in hot air at 70°–80° C.

Medium yield: kg 79.

Recovering Dimethylacetamide From Mother Waters and Washing Waters

Charge a glass lined vessel with mother waters and washing waters. Distil under vacuum (15–50 mmHg), at the temperature of 50°–80° C. The dimethylacetamide so distilled, after analytical control, may be used for subsequent preparation or stored.

iii) Diacerein Second Purification

100 Kg of diacerein coming from the first purification method are again crystallized from dimethylacetamide as described in passage ii).

The product is dired in hot air at 70°–80° C.

Medium yield: kg 90.

Dimethylacetamide can be recovered from mother waters and washing waters as above described.

iv) Diacerein Third Purification

Charge a 1500 l glass lined vessel with kg 100 of diacerein purified according to the second purification method (step iii) of the instant Example), kg 400 of virgin or recovered dimethylacetamide and kg 6 of acetic anhydride. If recovered dimethylacetylamide with moisture between 0.3% and 2% is used, add kg 6.6 of acetic anhydride for each kg of water contained in dimethylacetamide. Stir for 50 minutes at 25°–30° C., heat up to 100° C. and keep this temperature for 15 minutes. Filter through a pressure filter, rinsing the apparatus with kg 37.5 of virgin or recovered dimethylacetamide. Cool to 0°–2° C., keep this temperature for 2 hours and centrifuge the product, collecting mother waters into a proper container. Dry at the most and abundantly wash with filtered deionized water to eliminate at the most dimethylacetamide.

The product so obtained is dried under vacuum at 60°–65° C. or used as it is for the treatment with ethyl alcohol.

Medium yield: kg 95.5.

Dimethylacetamide can be recovered from mother waters and washing waters as above described.

v) Treatment with Ethyl Alcohol

This treatment is carried out to eliminate at the most the dimethylacetamide contained in diacerein.

Charge a 1500 l glass lined vessel with diacerein coming from the third purification method (step iv) of the instant Example and obtained from kg 100 of diacerein coming from the second purification method (step iii) of the instant Example and kg 350 of filtered virgin or recovered ethyl alcohol with maximum moisture of 5%. Heat up to reflux and keep for 1 hour. Cool to 0°–2° C., keep this temperature for 1 hour, centrifuge the product, and dry at the most.

Abundantly wash with filtered deionized water to eliminate at the most ethyl alcohol.

The product so obtained is dried in hot air at 70°–80° C. Medium yield: kg 95.

Recovery of Ethyl Alcohol From Centrifugation Mother Waters

Charge a proper vessel with centrifugation mother waters and distil ethyl alcohol at atmospheric pressure up to the temperature of 80° C. Ethyl alcohol so distilled, after analytical control, may be used for subsequent preparations or stored.

I claim:

1. A process for the preparation of 1,8-diacetoxy-3-carboxyanthraquinone of formula (I)

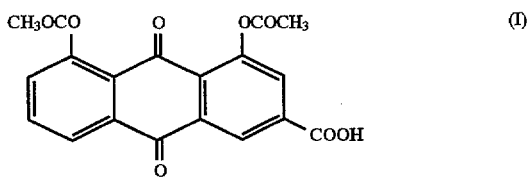

comprising:

a) acetylation of aloin of formula II (II)

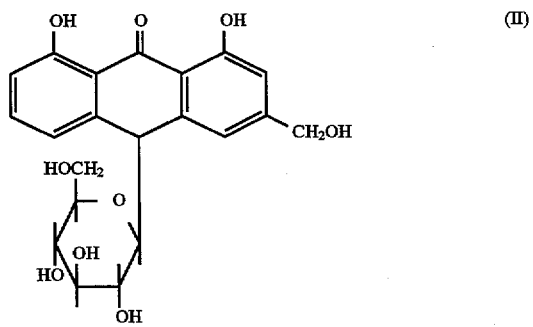

by treatment with an acetylating agent in a diluent, in the presence of a base or of an acid as catalyst to obtain the corresponding acetylated product as per formula (III)

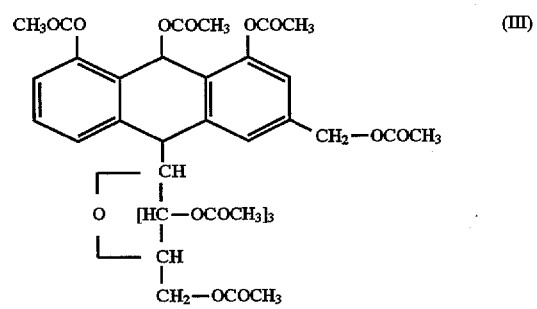

b) treatment of acetylated product (III) with an oxidizing agent, to give raw diacerein;

c) purification of raw diacerein,
wherein purification of raw diacerein comprises at least one crystallization step from a solvent selected from the group consisting of 2-methoxyethanol and N,N-dimethylacetamide, and optionally, a salification step comprising dissolving diacerein in a halogenated hydrocarbon solvent by salifying it with triethylamine, removing the insoluble residue, precipitating diacerein in aqueous acidic medium, recovering and drying the precipitated diacerein.

2. The process according to claim 1, wherein the raw diacerein coming from the oxidation step is first purified by means of the salification step, using methylene chloride as the halogenated solvent, then is crystallized from 2-methoxyethanol, and from anhydrous N,N-dimethylacetamide.

3. The process according to claim 1, wherein methylene chloride is used as the halogenated solvent, triethylamine is used in amounts ranging from 1 to 1.3 moles per mole of diacerein, the salification step is carried out at a temperature of from 15° C. to 30° C., the precipitation of diacerein in aqueous acidic medium is effected by adding concentrated aqueous hydrochloric acid.

4. The process according to claim 1, wherein the acetylating agent is acetic anhydride.

5. The process according to claim 1, wherein the acetylating agent is excess acetic anhydride used as a diluent.

6. The process according to claim 4, wherein acetylation is carried out in the presence of sodium acetate.

7. The process according to claim 6, wherein the amount of sodium acetate ranges from about 1% to about 10% in moles with respect to aloin.

8. The process according to claim 1, wherein acetylation is carried out at a temperature ranging from about 30° C. to about 150° C.

9. The process according to claim 5, wherein acetylation is carried out at the boiling temperature of the reaction mixture.

10. The process according to claim 1, wherein the oxidizing agent is chromic anhydride, used in glacial acetic acid.

11. The process according to claim 10, wherein chromic anhydride is used in amounts ranging from about 5 to about 15 moles per mole of initial aloin.

12. The process according to claim 11, wherein chromic anhydride is used in amounts ranging from about 7 to about 9 moles per mole of initial aloin.

13. The process as claimed in claim 10, wherein the reaction temperature ranges from about 0° C. to about 100° C.

14. The process as claimed in claim 10, wherein the reaction temperature ranges from about 20° C. to about 70° C.

15. The process according to claim 1, wherein the oxidation step is carried out after acetylation, without isolating the acetylated intermediate.

16. The process according to claim 10, wherein the reaction mixture coming from the acetylation is filtered and mixed, at a temperature of from about 60° C. to about 70° C., with mixture prepared by mixing water (in an amount not exceeding the stoichiometric amount of the acetic anhydride present in the reaction medium) with chromic anhydride and glacial acetic acid.

17. The process according to claim 16, wherein the water is in an amount of half the stoichiometric amount of the acetic anhydride present in the reaction medium.

18. The process according to claim 10, wherein after addition of chromic anhydride and glacial acetic acid, the reaction mixture is kept at about 60° to about 70° C., then cooled to about 20° to about 25° C., kept at this temperature for at least 6 hours, and then diacerein is recovered, washed with aqueous acetic acid, and dried.

19. The process according to claim 1, wherein raw diacerein coming from the oxidation step is dried up to a maximum water content lower than 1%.

20. The process according to claim 1 wherein before the crystallization steps, diacerein is dried up to a loss on drying value below 0.5%.

21. The process according to claim 1, wherein crystallization comprises dissolving diacerein in the selected solvent by heating the solvent/diacerein mixture, then precipitating the diacerin by cooling.

22. The process according to claim 21, wherein the solvent/diacerein mixture is heated to temperatures of about 75° to about 125° C., and precipitation is achieved by cooling the organic solution to temperatures of about 0° C. to about 5° C.

23. The process according to claim 1, wherein the purification is effected by subjecting diacerein to three successive crystallizations from anhydrous N,N-dimethylacetamide.

24. The process according to claim 23, wherein N,N-dimethylacetamide is in admixture with acetic anhydride.

25. The process according to claim 23, wherein anhydrous N,N-dimethylacetamide has a water content lower than 0.2%.

26. The process according to claim 23, which further comprises crystallization from ethanol.

27. The process according to claim 26, wherein ethanol has a maximum moisture content of 5%.

28. The process according to claim 23, wherein the three successive crystallizations from N,N-dimethylacetamide are carried out using mixtures of anhydrous N,N-dimethylacetamide and acetic anhydride in the ratio of about 400 to 6 by weight and are followed by a crystallization from ethanol with a maximum moisture content of 5%.

29. Process for purifying diacerein comprising crystallization of raw diacerein from a solvent selected from the group consisting of 2-methoxyethanol and N,N-dimethylacetamide.

30. A process for producing diacerein comprising acetylation of aloin to produce a compound of formula (III),

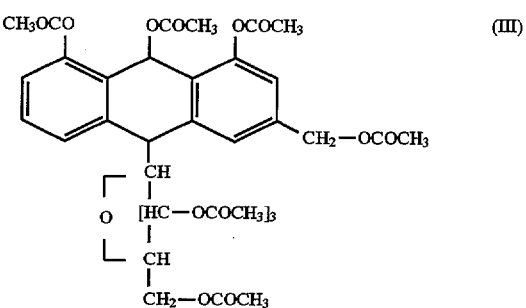

and reacting the acetylated compound of formula (III) with an oxidizing agent.

* * * * *